United States Patent [19]
Paez et al.

[11] Patent Number: 5,981,421
[45] Date of Patent: Nov. 9, 1999

[54] CATALYST SYSTEM FOR SELECTIVE HYDROGENATION OF HETEROAROMATIC SULFUR-CONTAINING AND NITROGEN-CONTAINING COMPOUNDS, AND PROCESS FOR PREPARING AND USING SAME

[75] Inventors: Daniel E. Paez, Edo. Miranda; Antida Andriollo, Caracas; Roberto A. Sanchez-Delgado, Caracas; Norma del V. Valencia, Caracas; Roberto E. Galiasso; Francisco A. Lopez, both of Edo Miranda, all of Venezuela

[73] Assignee: Intevep, S.A.

[21] Appl. No.: 09/004,119

[22] Filed: Jan. 7, 1998

Related U.S. Application Data

[62] Division of application No. 08/657,960, Jun. 4, 1996, Pat. No. 5,753,584.

[51] Int. Cl.⁶ .............................. B01J 31/02; B01J 31/28; B01J 31/24; B01J 31/30
[52] U.S. Cl. .................. 502/162; 502/151; 502/152; 502/155; 502/168; 502/169; 502/171
[58] Field of Search .................... 502/151, 171, 502/162, 152, 155, 168, 169

[56] References Cited

U.S. PATENT DOCUMENTS

| | | | |
|---|---|---|---|
| 3,679,688 | 7/1972 | Fenton | 260/290 P |
| 3,679,689 | 7/1972 | Fenton | 260/290 H |
| 3,857,895 | 12/1974 | Booth | 260/604 HF |
| 4,195,184 | 3/1980 | Kesling, Jr. et al. | 560/207 |
| 4,415,500 | 11/1983 | Manassen et al. | 502/167 |
| 4,517,390 | 5/1985 | Russell et al. | 585/277 |
| 4,925,990 | 5/1990 | Grosselin et al. | 568/862 |
| 5,003,110 | 3/1991 | Grosselin | 568/434 |
| 5,041,228 | 8/1991 | Herrmann et al. | 502/22 |
| 5,057,618 | 10/1991 | Herrmann et al. | 556/21 |
| 5,103,065 | 4/1992 | Bertleff et al. | 568/300 |
| 5,215,667 | 6/1993 | Livingston, Jr. et al. | 210/651 |
| 5,223,648 | 6/1996 | Herrmann et al. | 502/166 |
| 5,254,763 | 10/1993 | Gill et al. | 585/269 |
| 5,347,045 | 9/1994 | Herrmann et al. | 562/35 |
| 5,565,398 | 10/1996 | Herrmann et al. | 502/166 |
| 5,753,584 | 5/1998 | Paez et al. | 502/152 |

*Primary Examiner*—Elizabeth D Wood
*Attorney, Agent, or Firm*—Bachman & LaPointe, P.C.

[57] ABSTRACT

A catalyst system for selective hydrogenation of sulfur-containing and nitrogen-containing compounds of a heteroaromatic organic phase includes a mixture of a noble metal selected from Group VIII of the Periodic Table of Elements and a water-soluble ligand. A process for preparing the catalyst system and hydrogenation process using the catalyst system are also provided.

15 Claims, No Drawings

CATALYST SYSTEM FOR SELECTIVE HYDROGENATION OF HETEROAROMATIC SULFUR-CONTAINING AND NITROGEN-CONTAINING COMPOUNDS, AND PROCESS FOR PREPARING AND USING SAME

This is a Division, of application Ser. No. 08/657,960, filed Jun. 4, 1996, now U.S. Pat. No. 5,753,584.

BACKGROUND OF THE INVENTION

The invention relates to a catalyst system, a process for preparing the catalyst system, and a process for hydrogenating heteroaromatic compounds containing nitrogen and sulfur using a catalyst system.

The removal of sulfur and nitrogen contaminants from petroleum derivatives, especially without a reduction of octane number, is of critical importance in the oil industry. Although numerous methods and catalysts have been disclosed for use in removing sulfur and nitrogen, the need remains for a catalyst system which is useful for selective hydrogenation of aromatic compounds containing sulfur and nitrogen in order to convert refractive aromatic compounds into labile aromatic compounds.

It is therefore the primary object of the present invention to provide a catalyst system which is selective to hydrogenation of aromatic compounds containing sulfur and nitrogen.

It is a further object of the present invention to provide a catalyst system for selective hydrogenation of sulfur and nitrogen compounds, which catalyst system is water-soluble.

It is a further object of the present invention to provide a catalyst system which can be formed in situ at the site of reaction or hydrogenation.

It is another object of the present invention to provide a process for preparing a catalyst system in accordance with the invention.

It is still another object of the present invention to provide a process for selective hydrogenation of aromatic compounds containing sulfur and nitrogen using a catalyst system according to the present invention.

Other objects and advantages of the present invention will appear hereinbelow.

SUMMARY OF THE INVENTION

In accordance with the present invention, the foregoing objects and advantages are readily attained.

According to the invention, a catalyst system is provided for selective hydrogenation of sulfur-containing and nitrogen-containing compounds of a heteroaromatic organic phase, wherein the catalyst system comprises a mixture of a noble metal selected from group VIII of the Periodic Table of Element and a water-soluble ligand. In further accordance with the invention, an organic nitrogen base may be included in the catalyst system so as to speed the hydrogenation reaction in the presence of the catalyst system of the present invention as will be further discussed below.

The noble metal is preferably selected from the group consisting of ruthenium, rhodium, palladium, iridium and mixtures thereof.

The water-soluble ligand is preferably a sulfonated aryl phosphine such as m-mono sulfonated triphenyl phosphine, tri (m-sulfonated) triphenyl phosphine and mixtures thereof, or biquinoline such as 2,2'-biquinoline-4,4'-dicarboxylic acid in dipotassium salt form, trihydrate; 2,2'-biquinoline-5,5'-disulfonated in disodium salt form, dihydrate and mixtures thereof.

In further accordance with the present invention, a process for preparing a catalyst system for selective hydrogenation of sulfur-containing and nitrogen-containing compounds of a heteroaromatic organic phase is provided which process comprises the step of forming a mixture of a noble metal selected from Group VIII of the Periodic Table of Elements and a water-soluble ligand in water so as to provide an aqueous catalyst system.

Still further according to the invention, a process for selective hydrogenation of sulfur-containing and nitrogen-containing compounds from a heteroaromatic organic phase is provided, which process comprises reacting the organic phase with hydrogen in the presence of a catalyst system comprising a mixture of a noble metal selected from group VIII of the Periodic Table of Elements and a water-soluble ligand at reaction conditions so as to selectively hydrogenate sulfur-containing and nitrogen-containing compounds from the organic phase.

DETAILED DESCRIPTION

The present invention relates to a catalyst system for selective hydrogenation of sulfur-containing and nitrogen-containing compounds of a heteroaromatic organic phase. The catalyst system of the present invention is a water-soluble mixture of a noble metal selected from Group VIII of the Periodic Table of Elements and a water-soluble ligand.

In accordance with the invention, the water-soluble catalyst system may be dissolved into an aqueous solution which solution is mixed with an organic phase containing the sulfur-containing and nitrogen-containing compounds to be hydrogenated, and the reaction mixture so obtained is then exposed to hydrogen under hydrogenation conditions so as to selectively hydrogenate the sulfur and nitrogen compounds without significantly adversely affecting the octane number of the organic phase.

The noble metal of the catalyst system of the present invention is preferably selected from the group consisting of ruthenium, rhodium, palladium, iridium, platinum and mixtures thereof. The noble metal for use in the catalyst system of the present invention may preferably be provided in the form of a water-soluble salt, most preferably a chloride, bromide or iodide salt, and may alternatively be provided as a water-soluble organometallic compound as will be further discussed below.

The water-soluble ligand of the present invention may suitably be a sulfonated aryl phosphine such as m-monotrisulfonated triphenyl phosphine (TPPMS), most preferably in the sodium salt form, or tri (m-sulfonated) triphenyl phosphine (TPPTS). TPPMS may suitably be prepared in accordance with the procedure published by S. Ahrland, J. Chatt, N. Davies and A. Williams in *J. Chem. Soc.* (1958), page 276. TPPTS may suitably be prepared according to the invention by following the procedure described in French Patent No. 2,314,910, or as improved by the procedure described by T. Bartik, B. Bartic, B. E. Hanson, T. Glass, and W. Bebout in *Inorg. Chem.*, Volume 31 (1992), pages 2667–2670. Alternatively, the water-soluble ligand of the present invention may suitably be a biquinoline water-soluble ligand such as 2,2'-biquinoline-4,4'-dicarboxylic acid, dipotassium salt trihydrate, which is available from Aldrich Chemical Co., or 2,2'-biquinoline-5,5'-disulfonated, disodium salt which may be prepared by controlled sulfonation of 2,2'-biquinoline with sulfuric acid and 30% SO$_3$ and following the details described by S. Anderson, E. C. Constable, K. R. Seddon, J. E. Turp, J. E. Barggott and M. J. Pilling in *J. Chem. Soc., Dalton Trans.*, (1985) 2247–2261.

In further accordance with the invention, the catalyst system may be provided with noble metal and at least a portion of the water-soluble ligand by providing the noble metal as an organometallic compound such as metal-trisacetylacetonate, metal-bisacetylacetonate and mixture thereof, which compounds include water-soluble ligand. This is advantageous in that the preparation of the catalyst system according to the invention can be simplified by performing the addition of a single ingredient to water, if desired.

In further accordance with the invention, an organic nitrogen base may be included in the catalyst system so as to speed the hydrogenation reaction in the presence of the catalyst system of the present invention as will be further discussed below. According to the invention, the organic nitrogen base may suitably be selected from the group consisting of aniline, quinoline, isoquinoline, tetrahydroquinoline, decahydroquinoline, acridine, piperidine, triethylamine and mixtures thereof. As will be set forth below, the organic nitrogen base serves to speed the hydrogenation reaction, although in some cases this acceleration of the process is not necessary. Thus, in accordance with the present invention, the organic nitrogen base may be desirable used as a co-catalyst additive to the catalyst system of the present invention.

In further accordance with the invention, it has been found preferable to provide noble metal and water-soluble ligand in the catalyst system of the present invention in a molar ratio of metal, measured as a salt, to water-soluble ligand of between about 1:1 to about 1:10 and more preferably between about 1:3 to about 1:6. Further, when an organic nitrogen base is to be used, it has been found advantageous to maintain a molar ratio of metal to organic nitrogen base of between about 1:1 to about 1:20, more preferably between about 1:2 to about 1:6, and further to provide and maintain a molar ratio of water-soluble ligand to organic nitrogen base of between about 1:1 to about 1:6, more preferable between about 1:2 to about 1:4.

As will be set forth below, the catalyst system of the present invention exhibits excellent selectivity toward the hydrogenation reaction of sulfur and nitrogen-containing compounds of heteroaromatic organic phase without reducing normal aromatic compounds such as benzene, toluene, naphthalene and the like.

The catalyst system of the present invention is designed to be used in a bi-phase system formed between two immiscible liquids. One liquid phase is water, in which the water-soluble catalyst system of the present invention is dissolved. The other liquid phase is an organic phase such as a hydrocarbon containing the unwanted sulfur and nitrogen contaminants which are to be hydrogenated in accordance with the present invention.

The catalyst system of the present invention may preferably be prepared in accordance with several methods. Each of these methods will be discussed below. It should of course be noted, however, that numerous alternative methods for preparing the catalyst system of the present invention could be provided.

In accordance with one embodiment of the invention, the source of noble metal, water-soluble ligand and nitrogen base may be added directly to the desired volume of water, preferably adding each component one at a time while the water solution is subjected to continuous stirring.

In accordance with an alternative embodiment, the catalyst system of the present invention may be prepared by dividing the desired amount of water into separate volumes, preferably separate equal volumes, and preparing two aqueous solutions. The first aqueous solution is prepared using the source of noble metal, while the second aqueous solution is prepared using the water-soluble ligand. The metal aqueous solution is then added to the ligand aqueous solution, again during continuous stirring. In accordance with this embodiment, the organic nitrogen base is preferably added after the first solution is completely added to the second solution.

In accordance with another embodiment of the present invention, the catalyst system may suitably be prepared similar to that described above, with the exception that the ligand aqueous solution is added to the metal aqueous solution. This method of preparation has been found to provide excellent conversion of nitrogen and sulfur contaminants as will be demonstrated below.

The different characteristics provided to the catalyst system of the present invention by each of the above preparation methods will be further illustrated in the examples set forth below.

After formation of the catalyst system of the present invention it is preferable, and enhanced hydrogenation activity is provided, if the catalyst system is activated so as to form active species within the catalyst system as desired. The catalyst system of the present invention may suitably be activated by forming the aqueous solution containing the catalyst system by one of the methods discussed above, and exposing the aqueous catalyst system to hydrogen at hydrogenation pressure and temperature, preferably between about 40° C. to about 140° C. and 100 psi to about 1500 psi.

In accordance with the invention, the aqueous catalyst system of the present invention may suitably be activated individually, prior to mixture with the organic phase to be treated, or alternatively the aqueous catalyst system of the present invention may be introduced substantially simultaneously into the reactor with the organic phase containing the aromatic sulfur and nitrogen to be reduced. When the aqueous catalyst system is introduced simultaneously with the organic phase, the bi-phase system is again subjected to hydrogenation conditions as set forth above, as well as stirring, preferably a vigorous stirring, so as to provide active species on the catalyst system as desired.

In accordance with the invention, the stirring has been found to be an important part of the catalyst system activation, and the more vigorous the stirring, the more efficient hydrogenation will be provided. Stirring is preferably conducted at a rate of between about 500 rpm to about 5000 rpm.

As set forth above, the catalyst system of the present invention is well suited for the selective hydrogenation of sulfur and nitrogen-containing compounds of a particular organic phase. The catalyst system is selected for the hydrogenation of aromatic compounds containing sulfur and nitrogen only. The catalyst system does not induce reduction of carbon-hydrogen aromatic compounds of a heteroaromatic organic phase. Further, the catalyst system does not enhance reduction of normal and desirable aromatic compounds such as benzene, toluene, naphthalene and the like. Thus, the catalyst system of the present invention is particularly well suited to use in hydrogenation reactions for organic phases such as any straight non-hydrogenated hydrocarbon such as decalin, hexane, n-decane, cyclohexane, and the like, or any FCC naphtha or other petroleum derivative. The catalyst system of the present invention is useful in hydrogenation of aromatic sulfur and nitrogen-containing compounds such as thiophenes, benzothiophenes and quinolines.

In use, the catalyst system of the present invention is provided in an aqueous solution as discussed above, and mixed with an organic phase at a ratio of aqueous phase-:organic phase in the range of between about 90:10 to about 10:90. The mixture of aqueous catalyst system and organic phase preferably further includes a molar ratio of sulfur-nitrogen compounds:catalyst system of between about 100:1 to about 5:1, a metal salt:water-soluble ligand molar ratio of between about 1:20 to about 1:1, and a metal salt:nitrogen base molar ratio of between about 1:10 to about 1:1.

The mixture of aqueous catalyst system and organic phase is preferably prepared in situ in accordance with the present invention by mixing the two immiscible phases on site in the reactor. As set forth above, the aqueous catalyst system is preferably activated, either prior to or during the introduction of organic phase. After suitable activation, the hydrogenation reaction is then carried out. During this reaction, the bi-phase aqueous catalyst system and organic phase mixture is exposed to hydrogen under hydrogenation conditions, preferably including a temperature between about 40° C. to about 140° C. and a pressure of between about 100 psi to about 1500 psi, so as to hydrogenate the organic phase, and thereby convert undesirable sulfur and nitrogen aromatic compounds as desired.

The catalyst system of the present invention can be used in the hydrogenation process described above according to the invention so as to treat organic phase containing aromatic sulfur in the range of between about 300 ppm to about 6000 ppm. Further, the catalyst system of the present invention is effective in treating organic phase containing nitrogen species such as quinolines and derivatives in amounts up to about 1500 ppm.

The following examples further illustrate the catalyst system, process for preparation and hydrogenation process of the present invention.

Unless indicated to the contrary, the hydrogenation processes of each of the following examples were carried out in a 300 ml autoclave, batch type, with mechanical stirring at 630 rpm and temperature controlled heating unit with a total reaction volume of 100 ml. After six hours of reaction for each process, the autoclave was allowed to cool to room temperature and was depresurized, and the organic phase was analyzed in a gas chromatography instrument, model Varian 3400. The reduction of the contaminant concentration was measured in mol against an internal standard using gas chromatography.

EXAMPLE 1

This example demonstrates the effectiveness of the catalyst system using three preparation methods in accordance with the present invention.

In accordance with a first method (method 1), ruthenium trichloride trihydrate, sodium salt of TPPMS and aniline were added to water. For a second method (method 2), aqueous solutions of the metal salt and TPPMS were prepared, the aqueous metal solution was added to the TPPMS solution, and the aniline was then added. For the third method (method 3), aqueous solutions were prepared as in method 2, with the exception that the TPPMS solution was added to the aqueous metal solution, and aniline was then added.

Six aqueous solutions were prepared using ruthenium trichloride trihydrate ($RuCl_3 \cdot 3H_2O$) sodium salt of m-monosulfonated triphenyl phosphine (TPPMS) and aniline as an organic nitrogen base.

Two solutions were prepared according to each of the methods 1, 2 and 3 described above. The six aqueous solutions were tested for hydrogenating two different contaminants, benzo[b]thiophene (BT) and quinoline (Qui), which were hydrogenated to their corresponding heteroaromatic rings as 2,3-dihydrobenzo[b]thiophene (DHBT), 1,2,3,4-tetrahydroquinoline (THQ) and using decalin as the organic phase. The aqueous solution-organic phase mixture was formed in each case with a relation of water:decaline of 1:1, a total volume of 100 ml, and a relation of contaminant:catalyst system of 50:1.

The process conditions were 1000 psi, 130° C., and 630 rpm, and the results are shown in Table 1 where An=aniline.

TABLE 1

| Test | Contamin | Catalyst System | Method | Product | % Conv. |
|------|----------|-----------------|--------|---------|---------|
| 1 | BT | $RuCl_3$ + 6TPPMS + 6An | 1 | DHBT | 18 |
| 2 | BT | $RuCl_3$ + 6TPPMS + 6An | 2 | DHBT | 22 |
| 3 | BT | $RuCl_3$ + 6TPPMS + 6An | 3 | DHBT | 80 |
| 4 | Qui | $RuCl_3$ + 6TPPMS + 6An | 1 | THQ | 76 |
| 5 | Qui | $RuCl_3$ + 6TPPMS + 6An | 2 | THQ | 95 |
| 6 | Qui | $RuCl_3$ + 6TPPMS + 6An | 3 | THQ | 100 |

As shown in Table 1, the catalyst system of the present invention selectively hydrogenates the aromatic molecules at the heteroaromatic rings. Also, the best results are obtained for each contaminant using method 3.

EXAMPLE 2

This example demonstrates activation of the catalyst system of the present invention using two different procedures. Two aqueous solutions were prepared, each comprising a solution of ruthenium salt and a solution of water-soluble TPPMS ligand, prepared according to method 3 of example 1 above, to which aniline was added as organic nitrogen base. The contaminant treated for in both solutions was benzo[b]thiophene (BT) in an organic phase of decaline. In test 1, the aqueous catalyst solution was introduced into the reactor under the following operating conditions: pressure: 1000 psi, temperature: 130° C. and stirring of 630 rpm, 6 hours reaction time. After one hour of activation, the organic phase was added to the reactor.

In test 2, the catalyst aqueous solution was introduced into the reactor together with the organic phase solution containing contaminant, under the same operation conditions of test 1. The reactor was closed and equilibrium of pressure and temperature was obtained after 45 minutes, at which time hydrogenation was commenced. The results are set forth in Table 2.

TABLE 2

| Test. N° | contaminant | catalyst system | water:Decalin | cont:cat ratio(mol) | product(s) | % Conv. |
|---|---|---|---|---|---|---|
| 1 | BT | RuCl$_3$ + 6TPPMS + 6An | 1:1 | 50:1 | DHBT | 100 |
| 2 | BT | RUCl$_3$ + 6TPPMS + 6An | 1:1 | 50:1 | DHBT | 100 |

As shown, both procedures yield excellent results. However, Test 1 proceeded at a higher rate than Test 2, which took two hours longer than Test 1 to obtain the same conversion percentage. Thus, activation of the aqueous solution separately serves to speed up the hydrogenation reaction.

EXAMPLE 3

This example illustrates hydrogenation of aromatics containing sulfur and nitrogen atoms using different water-soluble ligands and different Group VIII metals in accordance with the invention.

Seventeen aqueous solutions were prepared and tested for the hydrogenation of the contaminants benzo[b]thiophene (BT) and quinoline (Qui). For each of the aqueous solutions, an aniline organic base was used. The relation of water:decaline (organic phase) was 1:1, the ratio of contaminant:catalyst, in terms of mols, was 50:1. The process conditions were 1000 psi, 130° C. and 630 rpm. Table 3A shows the results of tests 1 to 8 including conversion percentage with the catalyst system using different water-soluble ligands. Table 3B shows the results of Tests 9 to 17 using different Group VIII metals, TPPMS as water-soluble ligand and aniline as organic nitrogen base.

TABLE 3A

| Test N° | contaminant | catalyst system | product | % Conv. |
|---|---|---|---|---|
| 1 | Qui | RuCl$_3$ + 6TPPMS | THQ | 100 |
| 2 | Qui | RuCl$_3$ + 6TPPTS | THQ | 67 |
| 3 | Qui | RuCl$_3$ + 6biquiSO$_3$ | THQ | 50 |
| 4 | Qui | RuCl$_3$ + 6biquiCO$_2$ | THQ | 42 |
| 5 | BT | RuCl$_3$ + 6TPPMS | DHBT | 80 |
| 6 | BT | RuCl$_3$ + 6TPPTS | DHBT | 38 |
| 7 | BT | RuCl$_3$ + 6biquiCO$_2$ | DHBT | 18 |
| 8 | BT | RuCl$_3$ + 6biquiSO$_3$ | DHBT | 22 |

TABLE 3B

| Test N° | contaminant | catalyst system | product | % Conv. |
|---|---|---|---|---|
| 9 | BT | RuCl$_3$ + TPPMS | DHBT | 40 |
| 10 | BT | RuCl$_3$ + TPPMS | DHBT | 42 |
| 11 | BT | RhCl$_3$ + 6TPPMS+ | DHBT | 50 |
| 12 | BT | PdCl$_2$((BCHD) + 6TPPMS | DHBT | 42 |
| 13 | BT | IrCl$_3$ + 6TPPMS | DHBT | 33 |
| 14 | Qui | RuCl$_3$ + TPPMS | THQ | 100* |
| 15 | Qui | RhCl$_3$ + 6TPPMS+ | THQ | 80 |
| 16 | Qui | PdCl$_2$((BCHD) + 6TPPMS | THQ | 100* |
| 17 | Qui | IrCl$_3$ + 6TPPMS | THQ | 58 |

In tests 14 and 16, the hydrogenation of quinoline was very fast; quinoline was consumed even before the catalyst system obtained chemical equilibrium. It can be seen from Tables 3A and 3B that the catalyst system of the present invention is active for the hydrogenation of the contaminants using a variety of ligands and metals.

EXAMPLE 4

This example illustrates the effect of the use of organic nitrogen base (ONB) as a co-catalyst with the catalyst system of the present invention. The organic nitrogen bases tested were: quinoline (Qui), aniline (An), isoquinoline (iQui), 1,2,3,4-tetrahydroquinoline (THQ), decahydroquinoline (DHQ), urea, acridine, piperidine and triethylamine (TEA). The tests were carried out under the following conditions: pressure, 1000 psi; temperature, 130° C.; ratio water:decalin, 1:1 (v/v), for a time of 6 hours and stirring, 630 rpm. The catalyst system formulation was: RuCl$_3$.3H$_2$O+6(TPPMS)+6 ONB.

TABLE 4

| Test N° | contaminant(s) | catalyst system | ONB | Cont:cat ratio(mol) | product(s) | % Conv. |
|---|---|---|---|---|---|---|
| 1 | BT | RuCl$_3$ + 6TPPMS + | NO ONB | 50:1 | DHBT | 42 |
| 2 | BT | RuCl$_3$ + 6TPPMS + | An | 50:1 | DHBT | 100 |
| 3 | BT | RuCl$_3$ + 6TPPMS + | Qui | 50:1 | DHBT | 100 |
| 4 | BT | RuCl$_3$ + 6TPPMS + | iQui | 50:1 | DHBT | 100 |
| 5 | BT | RuCl$_3$ + 6TPPMS + | THQ | 50:1 | DHBT | 88 |
| 6 | BT | RuCl$_3$ + 6TPPMS + | DHQ | 50:1 | DHBT | 78 |
| 7 | BT | RuCl$_3$ + 6TPPMS + | acridine | 50:1 | DHBT | 80 |
| 8 | BT | RuCl$_3$ + 6TPPMS + | piperidine | 50:1 | DHBT | 75 |
| 9 | BT | RuCl$_3$ + 6TPPMS + | UREA | 50:1 | DHBT | 75 |
| 10 | BT | RuCl$_3$ + 6TPPMS + | TEA | 50:1 | DHBT | 63 |

From Table 4 it can be observed that the catalyst system of the present invention has a good activity without the organic nitrogen base, and an even better activity when the organic base is added.

EXAMPLE 5

This example demonstrates the effect of the variation of concentration of the organic nitrogen base. The concentration of the base isoquinoline [iQui] is in reference to the concentration of the metal, in mol, according to the expression: $[ONB]:[RuCl_3.3H_2O]$. The conditions were: pressure, 500 psi $H_2$; temperature, 130° C.; stirring, 630 rpm; ratio water/decalin: 1:1 (v/v). The molar ratio of contaminant::catalyst was 25:1 for a time: 6 hrs.

TABLE 5

| Test N° | contaminant(s) | catalyst system | [iQui] (mol) | product | % Conv. |
|---|---|---|---|---|---|
| 1 | BT | $RuCl_3$ + 4TPPMS + iQui | 0 | DHBT | 18 |
| 2 | BT | $RuCl_3$ + 4TPPMS + iQui | 1 | DHBT | 10 |
| 3 | BT | $RuCl_3$ + 4TPPMS + iQui | 3 | DHBT | 69 |
| 4 | BT | $RuCl_3$ + 4TPPMS + iQui | 5 | DHBT | 100* |
| 5 | BT | $RuCl_3$ + 4TPPMS + iQui | 10 | DHBT | 100* |
| 6 | BT | $RuCl_3$ + 4TPPMS + iQui | 15 | DHBT | 100* |

In tests 4 to 6 the hydrogenation process was so fast it was measured in minutes.

EXAMPLE 6

This example demonstrates the hydrogenation process as a function of the concentration of Group VIII noble metal. The process conditions were: pressure, 500 psi $H_2$; temperature, 130° C.; stirring, 630 rpm; reaction time, 3 hours. The metal concentration was taken in relation to the concentration of the contaminant, both in mols. The catalyst system for this example was: $RuCl_3.3H_2O$, 4 BIQUIc (2,2'-biquinoline-5,5'-dicarboxylic acid dipotassium salt trihydrate), 5 THQ (1,2,3,4-tetrahydroquinoline). Table 6 shows the results obtained.

TABLE 6

| Test N° | contaminant(s) | catalyst system | [$RuCl_3$] (mol) | product(s) | % Conv. |
|---|---|---|---|---|---|
| 1 | Qui | $RuCl_3$ + 4BlQUIc + 5THQ | 1 | THQ | 20 |
| 2 | Qui | $RuCl_3$ + 4BlQUIc + 5THQ | 5 | THQ | 70 |
| 3 | Qui | $RuCl_3$ + 4BlQUIc + 5THQ | 8 | THQ | 66 |
| 4 | Qui | $RuCl_3$ + 4BlQUIc + 5THQ | 12 | THQ | 47 |
| 5 | Qui | $RuCl_3$ + 4BlQUIc + 5THQ | 25 | THQ | 38 |
| 6 | Qui | $RuCl_3$ + 4BlQUIc + 5THQ | 50 | THQ | 98 |

EXAMPLE 7

This example illustrates the hydrogenation of heteroaromatic compounds (BT) as a function of the concentration of water soluble ligand (WSL). The example was carried out in a reactor of 75 ml for a total volume of solution of 50 ml, the stirring was provided using a magnetic bar. The process conditions were 1000 psi and 130° C. during 4 hours of reaction. The results are set forth below in Table 7.

TABLE 7

| Test N° | contaminant(s) | catalyst system | [WSL] (mol) | Cont:cat ratio(mol) | product(s) | % Conv. |
|---|---|---|---|---|---|---|
| 1 | BT | $RuCl_3$ + TPPMS + 6Qui | 0 | 50:1 | DHBT | 18 |
| 2 | BT | $RuCl_3$ + TPPMS + 6Qui | 2 | 50:1 | DHBT | 23 |
| 3 | BT | $RuCl_3$ + TPPMS + 6Qui | 4 | 50:1 | DHBT | 53 |
| 4 | BT | $RuCl_3$ + TPPMS + 6Qui | 6 | 50:1 | DHBT | 65 |
| 5 | BT | $RuCl_3$ + TPPMS + 6Qui | 8 | 50:1 | DHBT | 67 |
| 6 | BT | $RuCl_3$ + TPPMS + 6Qui | 10 | 50:1 | DHBT | 46 |

The results showed that a molar concentration of WSL of between about 4 to about 8, was most effective for the hydrogenation process.

EXAMPLE 8

Hydrogenation of heteroaromatics was carried out using the catalyst system of the present invention and varying the amount of water in relation to the amount of organic phase (decalin). The water variation did not affect the total volume of solution of 100 ml, which was maintained by adding the quantity of organic phase required. Reaction conditions: time of reaction: 3 hours; pressure: 500 psi $H_2$; temperature: 130° C.; ratio water/decalin: variable (v/v); stirring: 630 rpm; molar ratio of contaminant to decalin, 25:1. The results are set forth below in Table 8.

TABLE 8

| Tests N° | contaminant(s) | catalyst system | [H$_2$O] (mL) | Cont:cat ratio(mol) | product(s) | % Conv. |
|---|---|---|---|---|---|---|
| 1 | BT | RuCl$_3$ + 4TPPMS + 5iQui | 25 | 25:1 | DHBT | 50 |
| 2 | BT | RuCl$_3$ + 4TPPMS + 5iQui | 35 | 25:1 | DHBT | 61 |
| 3 | BT | RuCl$_3$ + 4TPPMS + 5iQui | 50 | 25:1 | DHBT | 70 |
| 4 | BT | RuCl$_3$ + 4TPPMS + 5iQui | 70 | 25:1 | DHBT | 84 |

EXAMPLE 9

Hydrogenation of heteroaromatic contaminant (BT) using the hydrosoluble catalyst system of the present invention is effected using as metal source a soluble salt of the metal and also an organometallic compound. The hydrogenation of benzo[b]thiophene (BT) to 2,3-dihydrobenzo[b]thiophene (DHBT) was carried out as shown in TABLE 9. The catalyst system had the following molar ratio: Ru source+6 TPPMS+6 iQui. The reaction conditions: temperature, 130° C.; pressure, 500 psi H$_2$; stirring, 630 rpm, molar ratio of contaminant:catalyst system, 50:1; volume of aqueous to organic phase, 1:1 (v/v) for a total volume of 100 ml; reaction time, 6 hours.

TABLE 9

| Expt. N° | contaminant(s) | catalyst system (Metal source) | product(s) | % Conv. |
|---|---|---|---|---|
| 1 | BT | RuCl$_3$.3H$_2$O | DHBT | 100 |
| 2 | BT | RuBr$_3$.nH$_2$O | DHBT | 67 |
| 3 | BT | RuI$_3$.nH$_2$O | DHBT | 56 |
| 4 | BT | RuCl$_2$(MeCN)$_4$ | DHBT | 97 |
| 5 | BT | HRuCl(TPPMS)$_2$(iQui)$_2$ | DHBT | 100 |
| 6 | BT | [RuHCl(TPPMS)$_2$]$_2$ | DHBT | 100 |

As shown in Table 9, the various metal sources provide excellent results. Also, when metal is provided in organometallic form, water-soluble ligand and organic nitrogen base may already be present, as in tests 4 and 5, and addition of extra water-soluble ligand or ONB was not necessary.

EXAMPLE 10

This example demonstrates the effect that the pressure has on the hydrogenation of heteroaromatic contaminants, using the catalyst system of the present invention. For the hydrogenation process, the conditions were: temperature, 130° C.; RuCl$_3$ was used in trihydrate form; organic matrix, decaline; volume ratio water:decalin, 1:1 (v/v); total solution volume, 100 ml.

profile, during hydrogenation showed that the process was completed in minutes.

EXAMPLE 11

This example demonstrates the effect of temperature on hydrogenation using the hydrosoluble catalyst system of the present invention. In this example, the reaction conditions were similar to those of in Example 10, with the exception that pressure was maintained at 500 psi and the molar ratio of contaminant to catalyst system was 25:1. The results are shown in Table 11.

TABLE 10

| Test. N° | contaminant | catalyst system | PRESSURE (PSI) | Cont:cat ratio(mol) | product | % Conv. |
|---|---|---|---|---|---|---|
| 1 | BT | RuCl$_3$ + 6TPPMS + 6An | 1000 | 50:1 | DHBT | 100 |
| 2 | BT | RuCl$_3$ + 6TPPMS + 6An | 500 | 50:1 | DHBT | 52 |
| 3 | BT | RuCl$_3$ + 6TPPMS + 6An | 250 | 50:1 | DHBT | 37 |
| 4 | Qui | RuCl$_3$ + 6TPPMS + 6An | 1000 | 50:1 | THQ | 100* |
| 5 | Qui | RuCl$_3$ + 6TPPMS + 6An | 500 | 50:1 | THQ | 100* |
| 6 | Qui | RuCl$_3$ + 6TPPMS + 6An | 300 | 50:1 | THQ | 100* |
| 7 | Qui | RuCl$_3$ + 6IPPMS + 6An | 250 | 50:1 | THQ | 80 |
| 8 | Qui | RuCl$_3$ + 6IPPMS + 6An | 100 | 50:1 | THQ | 67 |

In tests 4, 5 and 6 the hydrogenation of quinoline was very rapid under the given conditions. An analysis of the reaction

TABLE 11

| Expt. N° | contaminant(s) | catalyst system | Temp(° C.) | Cont:cat ratio(mol) | product(s) | % Conv. |
|---|---|---|---|---|---|---|
| 1 | BT | RuCl$_3$ + 4TPPMS + 3 iQui | 80 | 25:1 | DHBT | 56 |
| 2 | BT | RuCl$_3$ + 4TPPMS + 3 iQui | 100 | 25:1 | DHBT | 76 |
| 3 | BT | RuCl$_3$ + 4TPPMS + 3iQui | 120 | 25:1 | DHBT | 87 |
| 4 | BT | RuCl$_3$ + 4TPPMS + 3 iQui | 130 | 25:1 | DHBT | 100 |
| 5 | BT | RUCl$_3$ + 4TPPMS + 3 iQui | 150 | 25:1 | DHBT | 68 |

EXAMPLE 12

This example illustrates the selectivity of the catalyst system of the present invention. Seven tests were conducted for hydrogenation of heteroaromatics in presence of other aromatic and olefinic compounds. The contaminants tested were: (BT) benzo[b]thiophene; (Qui) quinoline; (Th) thiophene; (Nap) Naphthalene; (CHD) 1,4-cyclohexadiene; (DCN) 1-Decene; (COD) 1,5-cyclooctadiene and (Bz) benzene. Products obtained were: (DHBT) 2,3-dihydrobenzo[b]thiophene; (THQ) 1,2,3,4-tetrahydroquinoline; (Nap) Naphthalene; (THTh) 2,3,4,5-tetrahydrothiophene; (CHN) Cyclohexane; (COT) cyclooctane. The results are set forth in Table 12 below.

EXAMPLE 13

In this example, hydrogenation of heteroaromatic compounds were carried out using different organic phases such as decaline (decahydronaphthaline), n-heptane, cyclohexene, n-octane, and naphtha from coking and cracking processes. The naphtha used as organic phases were obtained from Venezuelan refineries: Naphtha from FCC process from Amuay refinery with a sulfur content of 1,200 ppm (naphtha 1); a light cokification naphtha from Cardon refinery with a sulfur content of 1,700 ppm (naphtha 2); and a HDH(R) naphtha from a process for deep hydroconversion of heavy oil with a sulfur content of 4,500 ppm (naphtha 3). The process conditions were 1000 psi H2, temperature of

TABLE 12

| Expt. N° | contaminant(s) | catalyst system | Cont:cat ratio (mol) | product(s) | % Conv. |
|---|---|---|---|---|---|
| 1 | BT + Qui + Nap | RuCl$_3$ + 6TPPMS + 6An | 50:1 | DHBT + THQ + Nap | 100:100:0 |
| 2 | BT + Th + Nap | RuCl$_3$ + 6TPPMS + 6An | 5:1 | DHBT + THTh + Nap | 100:60:0 |
| 3 | BT + Th + Nap | RuCl$_3$ + 6TPPMS + 6An | 50:1 | DHBT + THTh + Nap | 100:9:0 |
| 4 | BT + Qui + CHD | RuCl$_3$ + 6TPPMS + 6An | 50:1 | DHBT + THQ + CHN | 80:100:60 |
| 5 | BT + Qui + DCN | RuCl$_3$ + 6TPPMS + 6An | 50:1 | DHBT + THQ + DCN | 70:100:9 |
| 6 | BT + Qui + COD | RuCl$_3$ + 6TPPMS + 6An | 50:1 | DHBT + THQ + COT | 90:100:17 |
| 7 | BT + Qui + Bz | RuCl$_3$ + 6TPPMS + 6An | 50:1 | DHBT + THQ + Bz | 98:100:0 |

As shown, the hydrosoluble catalyst system advantageously hydrogenates aromatic compounds containing sulfur and nitrogen atoms without reducing other aromatics such as benzene, toluene and naphthalene. In the presence of cyclic olefins or linear olefins the hydrogenation proceeds very rapidly while reducing the olefins only in small percentages.

130° C., and stirring of 520 rpm; reaction time, 6 hrs. Results are shown in Table 13.

TABLE 13

| Test. N° | contaminant(s) | catalyst system | organic matrix | Cont:cat ratio(mol) | product(s) | % Conv. |
|---|---|---|---|---|---|---|
| 1 | BT + Qui | RuCl$_3$ + TPPMS + 6An | decalin | 50:1 | DHBT + THQ | 90:100 |
| 2 | BT + Qui | RuCl$_3$ + TPPMS + 6An | Heptane | 50:1 | DHBT + THQ | 87:100 |
| 3 | BT + Qui | RuCl$_3$ + TPPMS + 6An | naphtha 1 | 50:1 | DHBT + THQ | 66:100 |
| 4 | BT | RuCl$_3$ + TPPMS + 6Qui | naphtha 2 | 5:1 | DHBT | 60 |
| 5 | BT | RuCl$_3$ + TPPMS + 6An | naphtha 3 | 50:1 | DHBT | 67 |
| 6 | BT | RuCl$_3$ + TPPMS + 6An | decane | 50:1 | DHBT | 78 |

As shown, excellent results are obtained in accordance with invention using each organic phase.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A process for preparing a catalyst system for hydrogenation of sulfur-containing and nitrogen-containing compounds, comprising the steps of forming a first mixture of a noble metal selected from Group VIII of the Periodic Table of Elements in water and a second mixture of a sulfonated aryl phosphine water-soluble ligand in water and thereafter mixing the first mixture and second mixture together so as to provide an aqueous catalyst system.

2. A process according to claim 1, further comprising the step of adding an organic nitrogen base to the aqueous catalyst system.

3. A process according to claim 1, wherein the step of forming the aqueous catalyst system comprises adding the first mixture to the second mixture.

4. A process according to claim 1, wherein the step of forming the mixture comprises adding the second mixture to the first mixture.

5. A process according to claim 1, wherein the forming step comprises providing a hydrogenation reactor and mixing the first and second mixtures in situ in said hydrogenation reactor under hydrogenation conditions.

6. A process according to claim 1, wherein the noble metal is selected from the group consisting of ruthenium, rhodium, palladium, iridium, platinum and mixtures thereof.

7. A process according to claim 1, wherein the noble metal is in the form of a noble metal compound selected from the group consisting of water soluble metal salts, organo metallic compounds and mixtures thereof.

8. A process according to claim 1, wherein the noble metal is in the form of a metal salt selected from the group consisting of chloride salt, bromide salt, iodide salt and mixtures thereof.

9. A process according to claim 1, wherein the noble metal is in the form of an organometallic compound containing at least a portion of the water-soluble ligand.

10. A process according to claim 9, wherein the organometallic compound is selected from the group consisting of metal-triacetylacetonate, metal-biacetylacetonate and mixture thereof.

11. A process according to claim 1, wherein the water-soluble ligand is a sulfonated triaryl phosphine selected from the group consisting of m-monosulfonated triphenyl phosphine, tri (m-sulfonated) triphenyl phosphine and mixtures thereof.

12. A process according to claim 11, wherein the sulfonated triaryl phosphine is in sodium salt form.

13. A process according to claim 1, wherein the water-soluble ligand is a biquinoline.

14. A process according to claim 13, wherein the biquinoline is selected from the group consisting of 2,2'-biquinoline-4,4'-dicarboxylic acid in dipotassium salt form, trihydrate; 2,2'-biquinoline-5,5'-disulfonated in disodium salt form, dihydrate and mixtures thereof.

15. A process according to claim 2 wherein the organic nitrogen base is selected from the group consisting of aniline, quinoline, isoquinoline, tetrahydroquinoline, decahydroquinoline, acridine, piperidine, triethylamine and mixtures thereof so as to provide an aqueous catalyst system.

* * * * *